United States Patent [19]

Taboada

[11] 4,068,956
[45] Jan. 17, 1978

[54] PULSED LASER DENSITOMETER SYSTEM
[76] Inventor: John Taboada, 159 Ebbtide, San Antonio, Tex. 78227
[21] Appl. No.: 677,588
[22] Filed: Apr. 16, 1976
[51] Int. Cl.² ............................................. G01N 21/22
[52] U.S. Cl. .................................................... 356/205
[58] Field of Search .............................. 356/204, 205

[56] References Cited
U.S. PATENT DOCUMENTS

| B 530,569 | 3/1976 | Milam et al. | 356/205 |
| 3,520,624 | 7/1970 | Johnson et al. | 356/205 |
| 3,560,098 | 2/1971 | Witte et al. | 356/205 |
| 3,725,204 | 4/1973 | Marshall et al. | 356/205 |
| 3,782,828 | 1/1974 | Alfano et al. | 356/75 |

Primary Examiner—Paul A. Sacher
Assistant Examiner—R. A. Rosenberger
Attorney, Agent, or Firm—Joseph E. Rusz; George Fine

[57] ABSTRACT

A pulsed laser densitometer system measures highly optically dense samples. A pulsed laser beam pulse is split so that part of the beam pulse is directed through an optical delay path. The delayed beam pulse is then brought into the same path as the beam pulse transmitted through the sample and both beam pulses are fed through a detector. The output of the detector contains the optical density information in the ratio of the pulse amplitude of the transmitted pulse to the delayed pulse.

2 Claims, 4 Drawing Figures

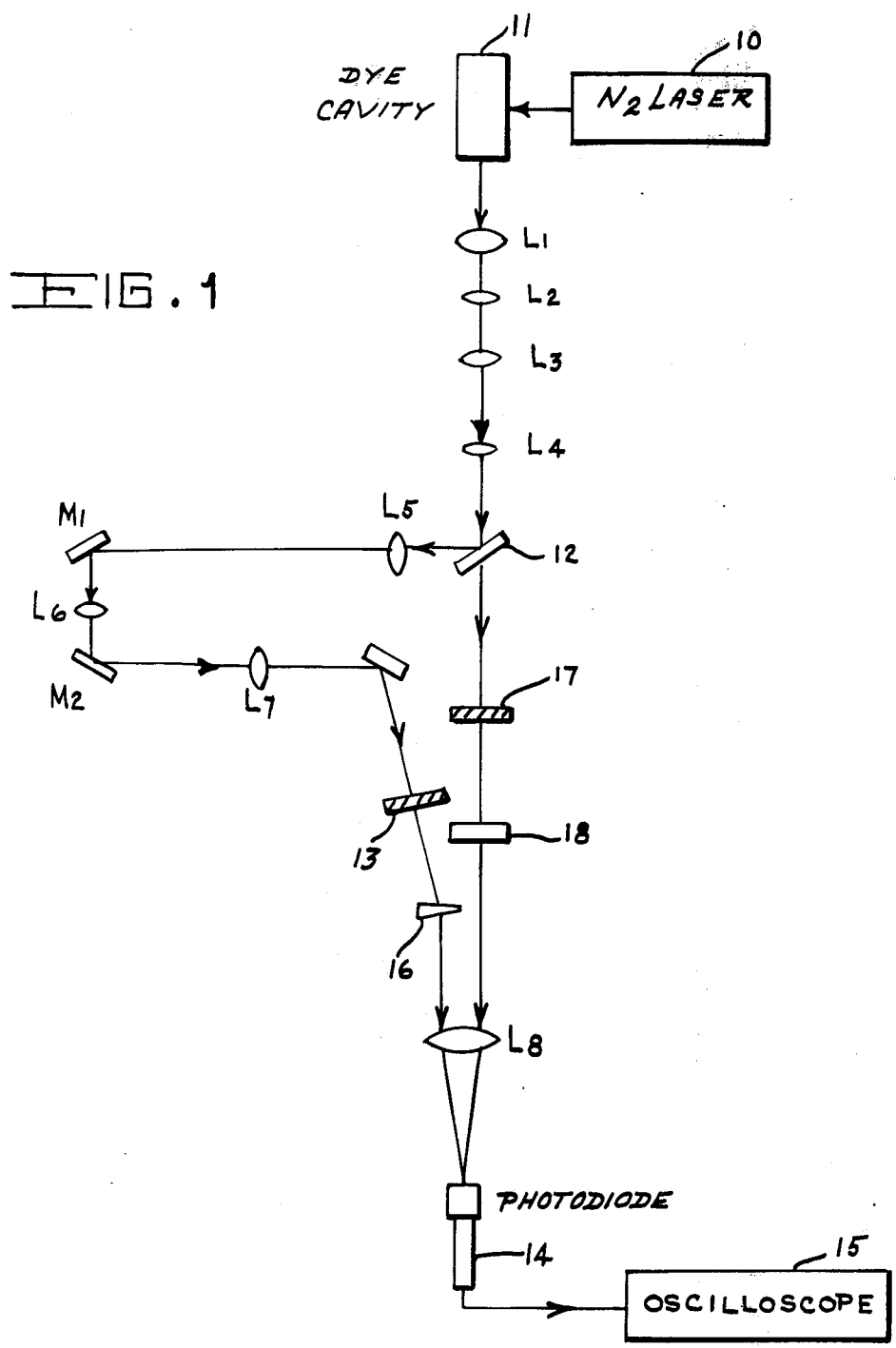

4,068,956

PULSED LASER DENSITOMETER SYSTEM

STATEMENT OF GOVERNMENT INTEREST

The invention described herein may be manufactured and used by or for the Government for governmental purposes without the payment of any royalty thereon.

BACKGROUND OF THE INVENTION

The present invention provides a relatively simple, easy and accurate method of measuring optical densities up to values of 10 or 11. This has previously not been possible. With existing densitometers, a density of 5 or 6 was the highest that could be measured, and the accuracy at high values was questionable. This invention has a potential for wide application in industries requiring accurate optical density values of materials with a high optical density and is equally applicable in all density (or transmission) measurements.

The present laser densitometer system is a substantial advancement in the state-of-the-art of spectrophotometric measurements of highly optically dense samples. Novel use is made of a single pulsed light source (such as a Q-switched laser or a pulse laser pumped dye line), and a single detector system. The invention permits the optical density measurement of very opaque samples having transmission values as low as $10^{-11}$. It can be readily automated and applied to scanning problems. A cost reduction over previous techniques is possible.

It is emphasized that laser sources are finding increasing application in spectroscopy because of their higher spectral brightness and purity. This invention is a spectrophotometric application where the laser's special temporal characteristics are also important, i.e., a simple and sensitive laser optical densitometer. The new densitometer uses a pulsed dye laser and an optical delay line.

The availability of intense laser light sources with a broad wavelength range, such as obtained from nitrogen laser pumped dye cavities, permits transmission spectrophotometry through very optically dense samples. Previously, conventional measurements required very sensitive differential techniques and stable sources. The particular advantages of a pulse nitrogen laser-pumped dye cavity in densitometry (e.g., Molectron UV-100 $N_2$ laser and Molectron Model DL-400 dye cavity) are the: high peak power ($\sim$ 50 kw); high pulse rate (50 Hz), and short pulse duration (5 to 10 ns). Possibly mode-locked cavities could also be applied as described subsequently; however, special instrumentation for adequate measurements of the ultra-short pulses would be required.

The nominal pulse duration of a pulsed dye laser is just sufficiently short to permit the construction of an optical delay of typical laboratory dimensions. In this specific example, an air path was used but optical fiber bundles can serve just as well. The delayed path is used for a reference signal in a transmission measurement, thus eliminating the need for an additional detector and subsequent precision control of the detector amplifier gain. A single laser pulse is used for both the probe and the reference. The laser stability, therefore, can be conveniently ignored.

Applications are immediate in the testing of eyewear for the protection against laser light. The present system permits a very accurate assay of the transmission properties of various optical filters and attenuators, and due to its high precision permits the monitoring of very small changes on a very dense sample as a function of various stresses such as chemical, heat, light, and aging. It allows the measurement of transmission of infrared (IR) or ultraviolet (UV) light pulses through aircraft windscreens. In the biomedical field, it will permit safe and convenient optical probing of the human body which can be modeled as a varying optical density filter and permit imaging by applying scanning techniques and thereby substitute x-ray methods.

SUMMARY OF THE INVENTION

A pulsed laser densitometer system is provided in which use is made of a single pulsed light source (such as a Q-switched laser or a pulse laser pumped dye laser), an optical delay line (through the use of mirrors or a fiber optic transmission line), and a single detector system. A light pulse of time duration ($t$) is incident on a sample for which the optical density is desired. Part of this incident beam, prior to entering the sample, is sent through an optical delay path length ($x$) which is nominally chosen to be given by the expression $x = 3ct$ where $c$ is the speed of light propagation in the delay medium which may be an optical fiber light pipe or a path between mirrors. This delay beam is brought into the same path as the beam transmitted through the sample which leads through a focusing lens onto a sufficiently sensitive and fast detector such as a photomultiplier, photodiode, photoresistor, etc. The output of the detector contains the optical density information in the ratio of the pulse amplitude of the transmitted pulse to the delayed reference pulse. The use of calibrated neutral density filters is readily introduced to permit the accurate balancing of this ratio for extremely wide disparities of 7 to 10 orders of magnitude. The pulse information can be displayed on an oscilloscope as two pulses separated in time by the value $t_d = x/c$, or the ratio can be measured by a time delayed dual channel box car integration of a series of such light pulse pairs. A prototype built for immediate Government use employing a photodiode and an oscilloscope for read-out has permitted measurement to 7.5 OD. An addition of a sensitive photomultiplier detector and a dual channel box car integrator should permit measurements up to 10 or 11 OD. Applications to in-vivo scanning densitometry of opaque biomedical entities such as the human chest and appendages can potentially be accomplished through the use of this concept.

DESCRIPTION OF THE DRAWINGS

FIG. 1 shows schematically a preferred embodiment of the pulsed laser densitometer system;

DETAILED DESCRIPTION OF THE PREFERRED EMBODIMENT

Figure 2A:
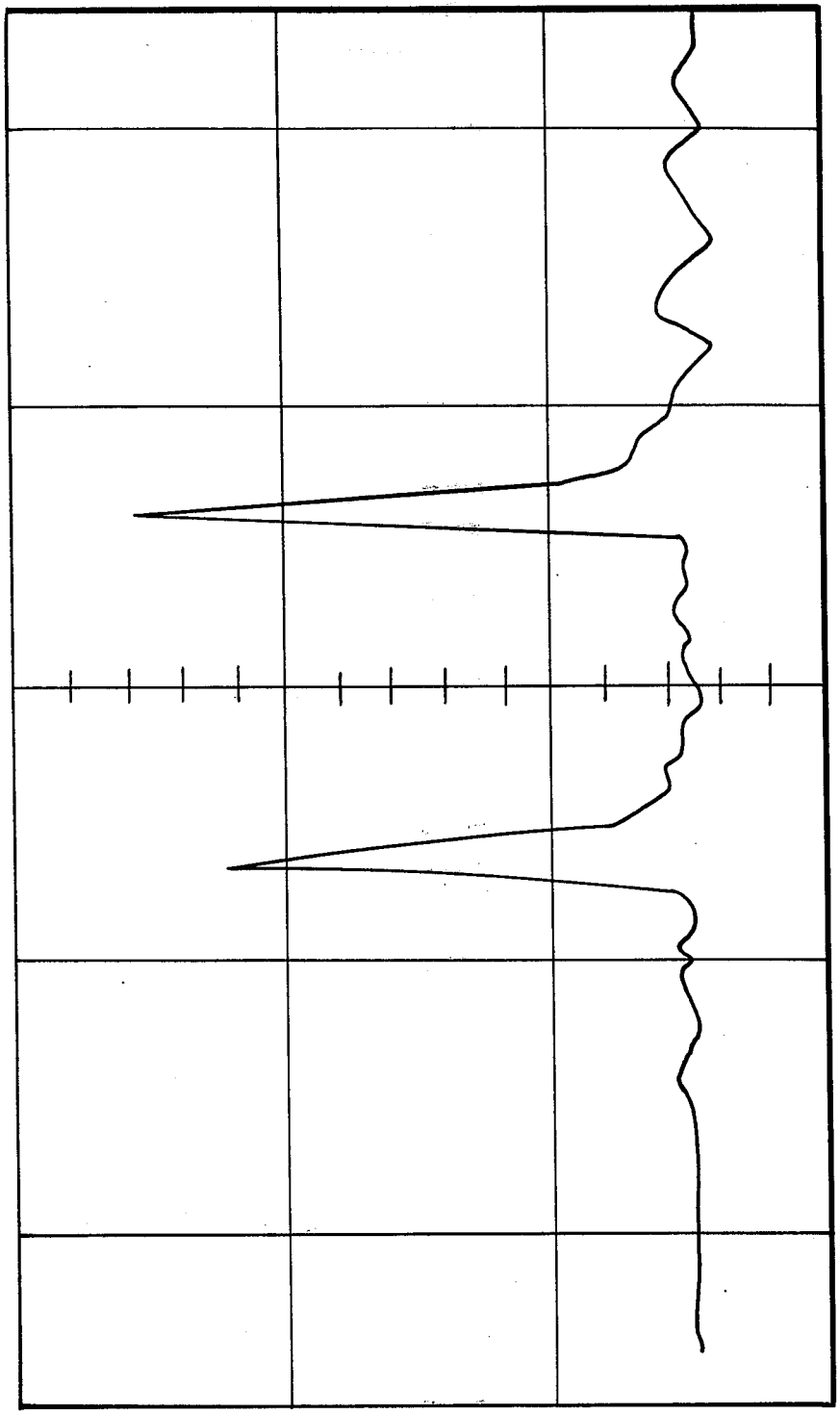
FIG. 2a shows typical pulse pairs utilizing one set of standardized filters.

Now referring to FIG. 1 in which the optical arrangement of the pulsed dye laser densitometer is shown schematically, pump laser 10 in this specific example is a TEA $N_2$ type (Molectron Model UV-1000). The output of pump laser 10 has a typical duration of approximately 10 ns and peak power of the order of 1 MW. This laser pumps a dye cell in separate cavity 11. Depending on the fluorescence lifetime of the dye, the pulse duration of dye cavity 11 will be of the order of 5–10 ns. Spatial asymmetry in the output beam is corrected with cylindrical lens L1 (−20 cm focal length). The beam is further controlled by a 1 m focal length relay lens L2 and by a collimating telescope consisting of lenses L3 (1 m) and L4 (8 cm). Beam splitter 12 (BS) separates the beam into a probe beam (transmitted) and a reference beam (∼ 10 percent partial reflection). The reference beam is delayed by means of the optical path between mirrors M1, M2, M3 arranged along a 5 m optical bench. Lenses L5, L6 and L7, each with everal meters of focal lengths) control the beam divergence. A total delay of about 53 ns is obtained from a 15.8 m path. This provides adequate temporal separation of the probe and reference pulses. Attentuation reference filter 13 of the reference beam reduces its signal to a convenient minimum detectable level at Spectra Physics 403 high speed photodiode detector 14 as observed with Hewlett Packard Model 184B high speed storage oscilloscope 15 with Model 1805A amplifier and Model 1825A time base. The reference beam is co-aligned with the probe beam by means of a wedge 16 and focused onto the detector by lens L8. A set of standardized filters (SF) 17 is initially introduced to match the minimum signal level of the reference. The focusing lens, L8, an achromat of 10 cm f.l., serves to project both the reference beam and the probe beam from sample holder 18, onto a small area of about 1 mm² on photodiode 14. This inhibits small gain variations fro different parts of the detector surface.

It is noted that although Spectra Physics 403 high speed photodiode detector 14 is utilized any similar conventional photodiode may be substituted. It is also indicated that a Hewlett Packard Model 184B oscilloscope is used. However, any similar conventional oscilloscope may be utilized in place thereof.

Figure 2B:
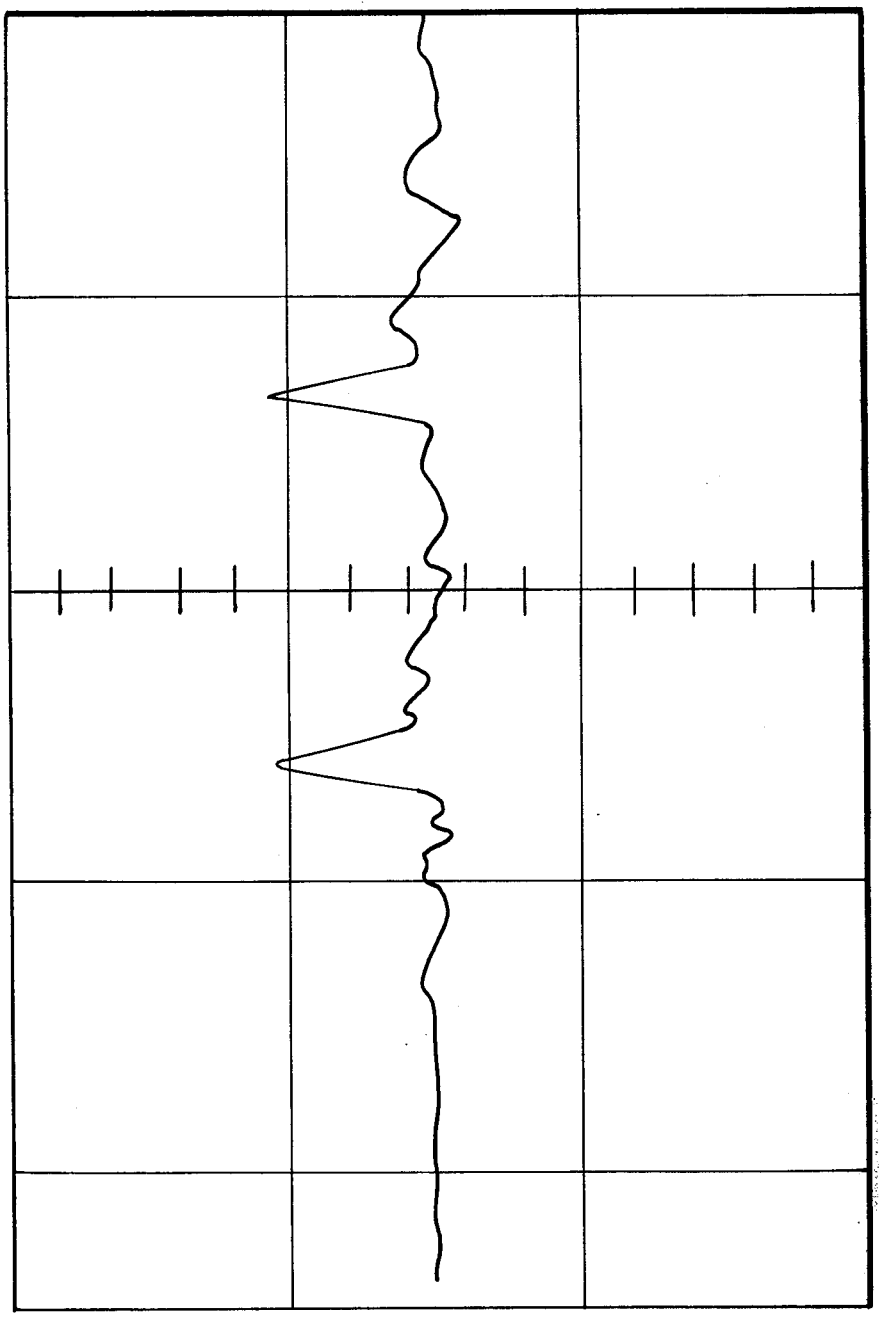
FIG. 2b shows typical pulse pairs with a second set of standardized filters.

With no sample in the beam, FIGS. 2a and 2b show typical pulse pairs observed with a balanced condition existing for the two beams at the detector. Standardized filters totaled 7.04 densities for FIGS. 2a and 7.5 densities for FIG. 2b. Thus, densities as high as 7.5 can be measured. Dye cavity output at 515 nm, obtained with 7-diethylamin 4-trifluoromethyl coumarin (7D4TMC), having a pulse duration of approximately 7 ns, and a peak power of 50 kw was used in the exxample, FIG. 2. The beam spot diameter in the same region was about 1.5 cm.

The optical density of an unknown sample placed in sample holder 18 is measured by removing standardized filters to obtain near balance of the pulse signals. The optical density of the unknown sample is given by the sum of the value of the standardized filters removed ($f_r$), and the negative $\log_{10}$ of the ratio of the probe pulse amplitude ($A_p$) to the reference pulse amplitude ($A_r$), i.e., $$O. D. = f_r - \log_{10}(A_p/A_r).$$

Figure 3:
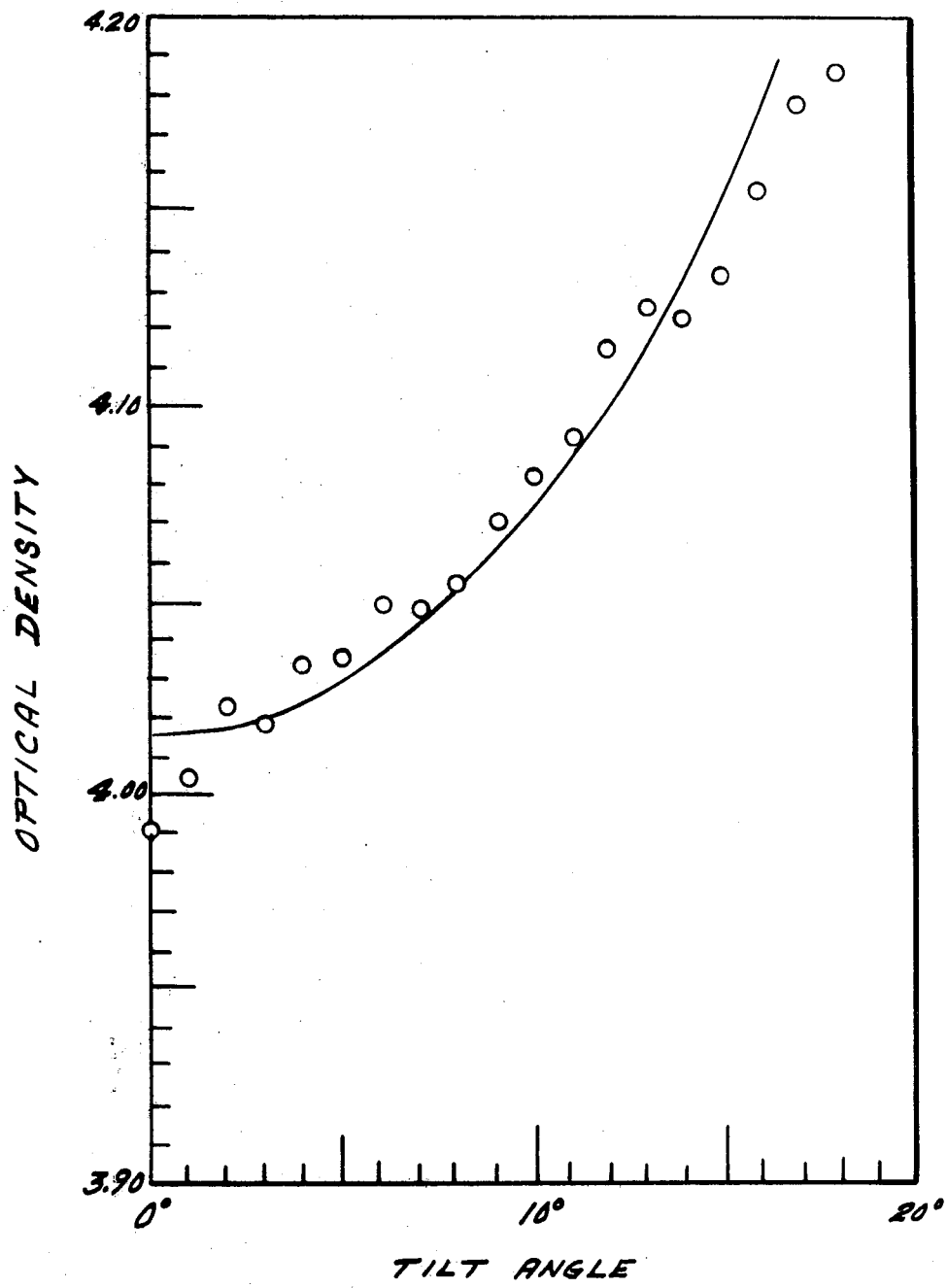
FIG. 3 shows the variation in density.

As a demonstration of the resolution of this approach, FIG. 3 shows the variation in density presented by a 4.015 O.D. neutral density filter having a thickness of 3.95 mm as it is tilted through a small angle. A fractional variation of 0.5 percent can be readily detected and an unusual effect on the propagation of light beams can be observed for highly absorbing materials, in that only an index of refraction of unity can account for the curve fit in the data.

Since this specific case of the nitrogen laser and most other lasers can be repetitively pulsed to rates as high as 50 Hz, signal averaging techniques can be applied to increase the sensitivity greatly. Such an approach might incorporate a high speed peak height detector with two sample-and-hold circuts synchronized with a precision electronic delay between them eqial to the optical delay. The output of the sample-and-hold circuits can be digitized and scaled in separate adder circuits for subsequent recision ratio computation. Alternatively, a commercially available dual channel box car integrator such as the Princeton Applied Research Model 162 can be applied to sampling the signal pulse then the reference pulse to compute the ratio after many pulse periods.

Automation is possible by replacing the neutral density standardized stack (SF) by a servo driven variable neutral density filter wheel, and connecting the output from the sampling circuits to a null or ratio-of-one detector. The position of the filter wheel is then the desired density if it is driven by the null or ratio-of-one detector.

Spectrophotometric scans can be obtained by using a wavelength scan on the dye laser source. By locking the servo driven neutral density filter as discussed above to the wavelength of a tunable pulsed dye laser a scan of the optical density versus wavelength is thus obtained.

Taking this system and introducing a highly directional detection system (which can readily be accomplished with laser sources) it is possible to scan the human body for transmission since the optical densities presented are within the range of this system.

What is claimed is:

1. A pulsed densitometer system for measuring a sample comprised of a pump laser of the TEA $N_2$ type, a dye cavity pumped by said pump laser to provide an output beam of pulses, the pulse duration of said dye cavity being of the order of 5–10 ns, a cylindrical lens for correcting the sssymetry of the output beam from said dye cavity, a combination of a focal length relay lens and a collimating telescope for further correcting the bam from said cylindrical lens, a beam splitter to separate the beam from said combination into a probe beam and a reference beam, means to delay said reference beam to provide temporal separation of said probe and reference beam, said delay means having a predetermined length $x$, $x$ being equal to $3ct$ with $c$ being the speed of light propagation in the delay means and $t$ being the pulse duration time, said delay means consisting of first, second and third mirrors in sequence and first, second and third lenses, each of said lenses with several meters of focal lengths to control the beam divergence, said first lens positioned between said beam splitter and said first mirror, said second lens between said first and second mirrors, said third lens between said second and third mirrors, an attenuation reference filter receiving the reference beam from said delay means for reduction to a minimum detectable level, a sample to be measured for density, said probe beam from said beam splitter passing therethrough, a focusing lens receiving the probe beam from said sample, a wedge receiving the reference beam from said attenuation reference filter to co-align said reference beam with said probe beam on said focusing lens, a high speed photodiode detector receiving the co-aligned probe and reference beam from said focusing lens in a small area thereupon of about 1 mm² to inhibit small gain variations from different parts of the detectors surface, an oscilloscope receiving the output from said high speed photodiode detector to provide the optical density information of said sample in the ratio of the pulse amplitude of the probe beam to the reference beam.

2. A pulsed densitometer system for measuring a sample as described in claim 1 wherein said collimating telescope consists of a pair of lenses.

* * * * *